(12) United States Patent
Hanley

(10) Patent No.: US 9,335,258 B2
(45) Date of Patent: May 10, 2016

(54) SYSTEM AND METHOD OF RETRIEVING MASS DENSITY DISTRIBUTIONS AND THERMAL PROFILES FROM THE ATMOSPHERE TO IDENTIFY MOLECULAR CONSTITUENTS THAT MAY ABSORB SPECTRAL ENERGY

(71) Applicant: Stephen T. Hanley, Portland, OR (US)

(72) Inventor: Stephen T. Hanley, Portland, OR (US)

(*) Notice: Subject to any disclaimer, the term of this patent is extended or adjusted under 35 U.S.C. 154(b) by 194 days.

(21) Appl. No.: 14/200,236

(22) Filed: Mar. 7, 2014

(65) Prior Publication Data

US 2014/0353531 A1    Dec. 4, 2014

Related U.S. Application Data

(60) Provisional application No. 61/828,892, filed on May 30, 2013.

(51) Int. Cl.
*G01N 21/59*    (2006.01)
*G01N 21/31*    (2006.01)

(52) U.S. Cl.
CPC ............................. *G01N 21/31* (2013.01)

(58) Field of Classification Search
CPC .... G01W 1/00; G01N 21/1702; G01N 21/31; G01N 21/59
USPC ......... 250/222.2, 226, 203.4, 214.1; 356/328, 356/326, 305
See application file for complete search history.

(56) References Cited

U.S. PATENT DOCUMENTS 6,734,966 B2 * 5/2004 McCarthy ............. G01J 3/2823
250/339.05

* cited by examiner

*Primary Examiner* — Que T Le
(74) *Attorney, Agent, or Firm* — Harpman & Harpman

(57) ABSTRACT

A system and method for the retrieval of mass density distributions or "profiles" for at least a portion of the Earth's atmosphere for one or more molecular constituent within the atmosphere that absorbs spectral energy. The spectral energy may be anywhere within wavelengths of radiation from UV through visible and into the infrared. The system incorporates a single ended instrument to permit continuous monitoring of the vertical profiles of all constituents of interest.

6 Claims, 4 Drawing Sheets

Figure 2. Spectral Window Selected For H2O Study
Transmission for a 65deg Slant Angle
—— Complex Inversion Test Profile ······· Mid Latitude Average Profile

SYSTEM AND METHOD OF RETRIEVING MASS DENSITY DISTRIBUTIONS AND THERMAL PROFILES FROM THE ATMOSPHERE TO IDENTIFY MOLECULAR CONSTITUENTS THAT MAY ABSORB SPECTRAL ENERGY

This application claims the benefit of U.S. Provisional Application No. 61/828,892, filed on May 30, 2013.

BACKGROUND OF THE INVENTION

1. Technical Field

This invention relates to measuring atmosphere constituent concentration profiles by use of analysis by spectrograph or other high resolution spectroscopic instrumentation.

2. Prior Art

Atmospheric constituent concentration profiles as well as temperature profiles may be measured from sea level to top of the atmosphere. These molecular constituents concentrations at all altitudes may be of interest to EPA or similar agencies in this and other countries for monitoring air quality and changes of important components of the atmosphere as they may relate to "climate change." The atmospheric constituent profiles and thermal profiles may also be of interest to the military or other agencies or organizations for impact on functioning of their Electro-Optical systems that may be terrestrially based or space based.

Conventional approaches to measuring the atmospheric constituent profiles have incorporated balloon borne sensors to sample the atmosphere as the balloon rises from the earth surface through the atmosphere. These balloon borne sensors are typically limited to one profile per release, and they may be expensive in terms of single use equipment as well as manpower. The profiles gathered by these conventional approaches may be limited by the balloon borne detector package utilized (such packages are typically limited to water vapor, temperature, and Barometric pressure).

Examples of such prior art approaches are illustrated in prior art U.S. Pat. Nos. 7,489,397, and 8,035,813.

U.S. Pat. No. 7,489,397 is directed to an instrument, system and method for automated low-cost atmospheric measurement utilizing a collective lens interconnected to a high resolution spectrometer by fiber optic cables. The system includes pan and tilt positioning abilities for tracking and azimuth angle of the sun to take readings in the so defined column ozone determination.

U.S. Pat. No. 8,035,813 claims a method and device for measuring emissions of gaseous substances to the atmosphere using scattered sunlight spectroscopy and optical measuring device including a telescope.

SUMMARY OF THE INVENTION

A system and method using a single ended instrument to continuously monitor vertical profiles for a plurality of constituents with retrieval of mass density distribution profiles for spectrograph analysis utilizing proprietary computer software for analysis of molecular absorption data and generated profile for desired atmospheric constituents by comparison to compiled date references.

DETAILED DESCRIPTION OF THE INVENTION

Figure 1:
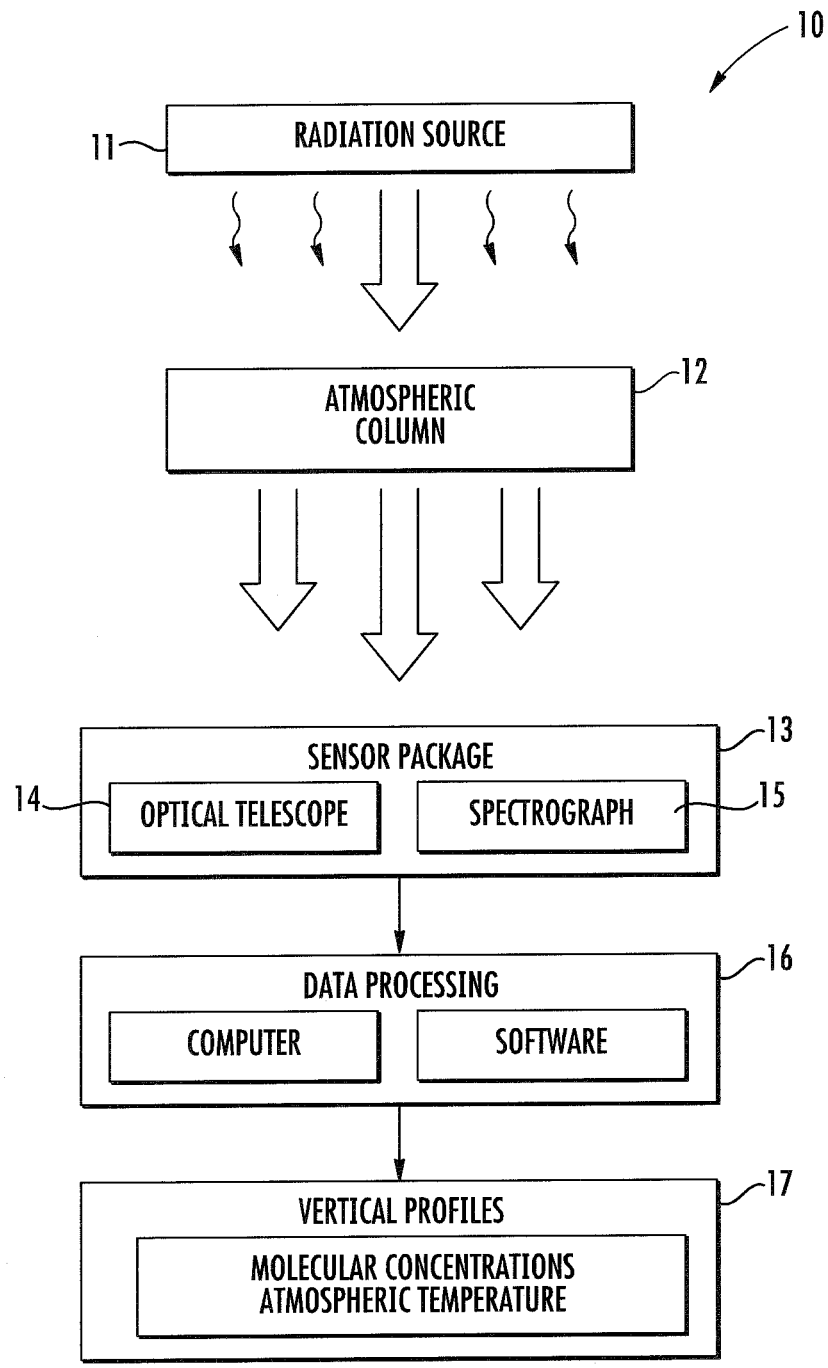
FIG. 1 is a block flow diagram illustrating the basic methodology of the method and system of the invention.
Figure 2:
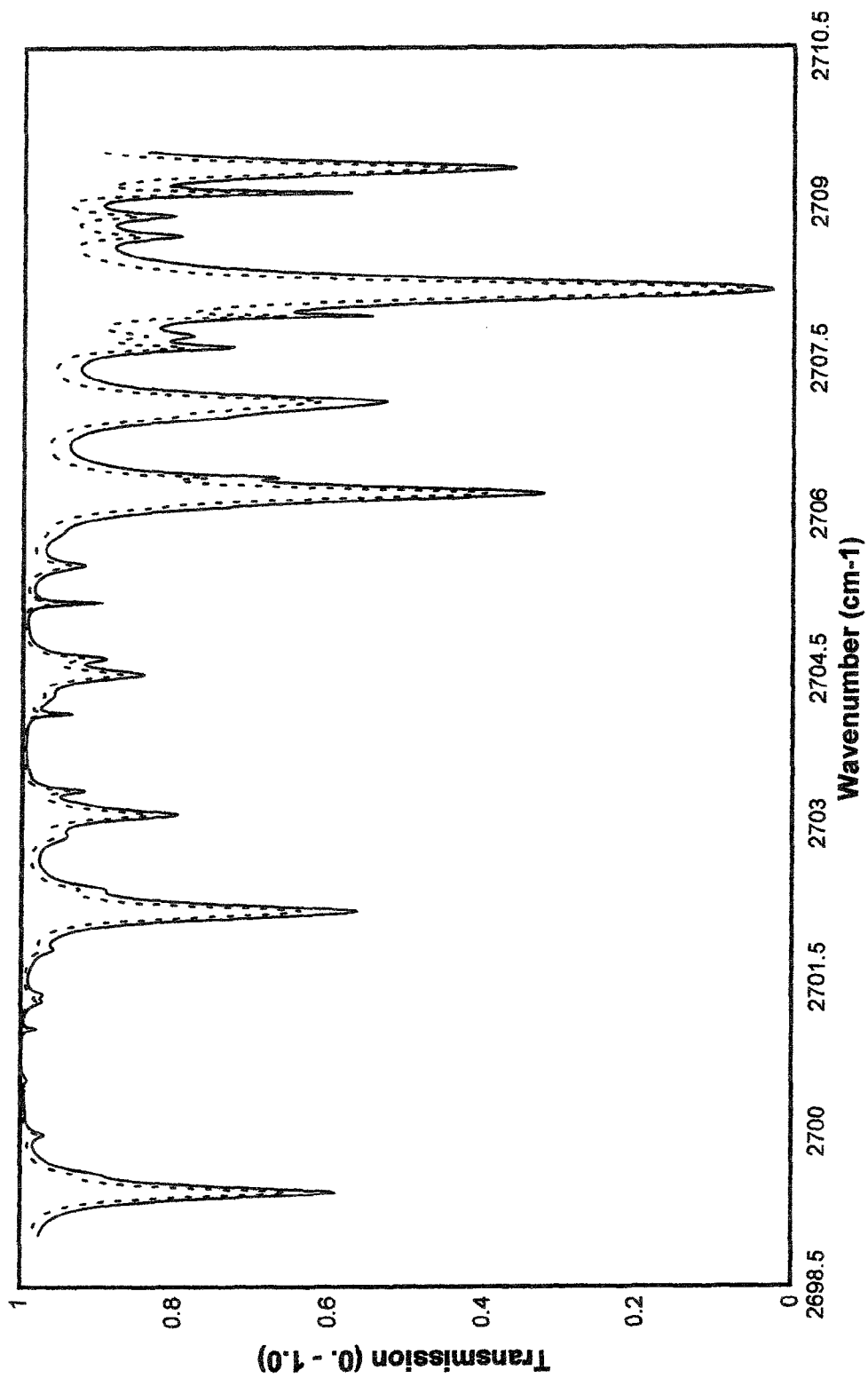
FIG. 2 is an example of system analysis using a graph of spectral window for H20 in inversion test profile.

Referring now to FIG. 1 of the drawings the methodology of the retrieval and analysis of atmospheric constituents system 10 of the invention is illustrated. A radiation source 11 such as the sun illuminates an atmospheric column 12 to be measured. A sensor package 13 provides collection and analysis by utilization of an optical telescope 14 fitted in this example with a high resolution spectrograph 15. Data processing 16 defines a computer-based software data processor to analyze molecular absorption data and generate a profile for the desired atmospheric constituent.

Figure 3:
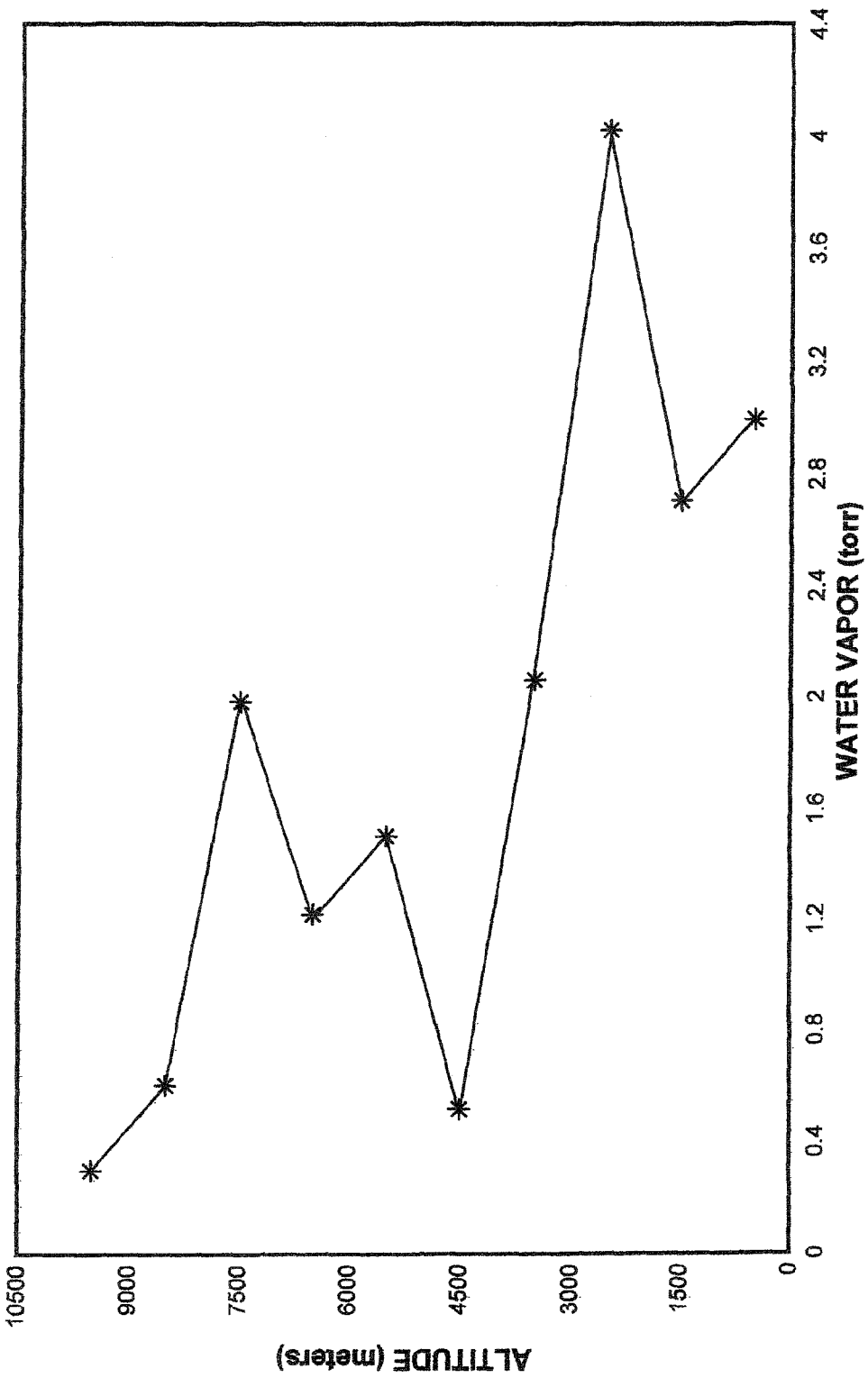
FIG. 3 is an example of system analysis graphic of retrieval vertical H20 profile of water vapor shown in XY axis.

It will be seen that atmospheric constituents profiles 17 are typically measured as concentration versus elevation from sea level (or some other portion of the earth's surface) to the top of the atmosphere; an example of which is charted in FIG. 3 of the drawings.

Atmospheric constituent profiles 17 are of interest to a variety of research and regulatory entities and/or agencies for monitoring air quality and changes of important components of the atmosphere as they may relate to climate change.

Atmospheric constituent profiles 17 may be derived from data relating to measuring high resolution transmission spectra in key spectral regions and applying specialized iterative retrieval process to these data. The steps used in the retrieval are to perform a high resolution line-by-line calculation of slant path transmission (widely available AFGL line atlas based HITRAN, or equivalent calculation) using a Mid Latitude "estimator vertical profile" as a starting point. Next the point-by-point differences between the calculated and measured spectra are noted. Adjustments are made to the initial Mid latitude estimator profile and a new calculated slant path spectrum is made. Then point-by-point differences between measured and calculated absorption detail are again examined. When the new point-by-point differences between measured and (most recently adjusted) estimator spectra are reduced, then the most recent adjusted profile (with improvement to spectral detail fit) becomes the new estimator reference. This process is repeated until no further improvement can be made between calculated and measured transmission curves, at which point a vertical profile has been retrieved. The system and method of the present invention 10 provides simplicity and ease of operation as well as permitting the collection of a more extensive data set that may be easier and more direct to analyze and interpret. These improvements may be enabled by a virtue of the improved system and method of the invention 10 incorporating a single ended operation using solar or other broadband radiation source 11 and improved data collecting and processing hardware package by providing a more capable, extensive and adaptable sensor package 16 and data collection and analysis packages.

The need or desire for multiple and/or continuous operation of sensors to build data sets that may address the information requirements to permit the desired level of analysis and the need for reference profiles, other than H20 may be expensive in terms of human and physical resources when utilizing conventional technology, such as aerial balloon releases.

Figure 4:
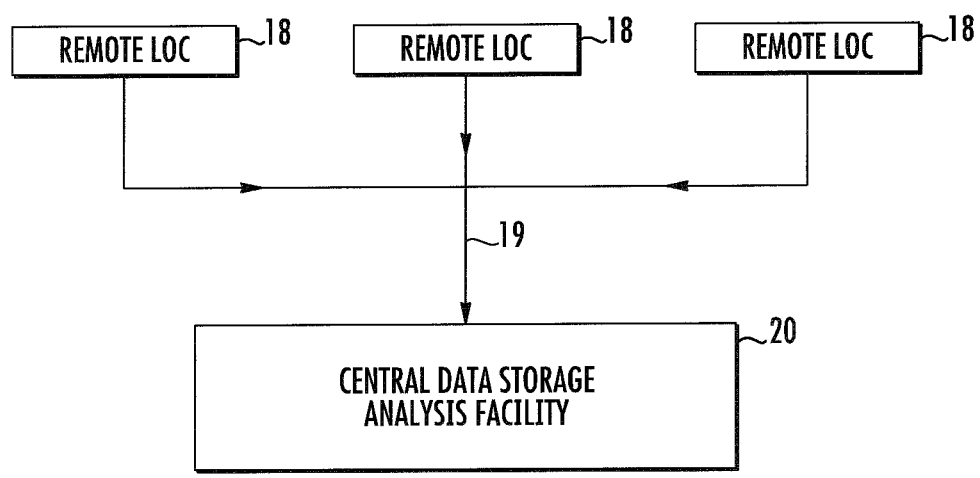
FIG. 4 is a block flow diagram illustrating applicable sensor deployment in a multi-diverse gathering array configuration.

It will be seen that the single ended instruments, such as that utilized in the system and method of the present invention, may be used to continuously monitor the vertical profile of any number of atmospheric constituents of interest. Also the system and method may incorporate a computer with specialized software that has been optimized in speed (coded in direct CPU machine language, and use of faster multiprocessor-core or multi-threaded devices, etc.), may be miniaturized for production and ruggedized and programmed to permit automated monitoring, data collection and data transmission at remote locations 18, as illustrated in FIG. 4 of the drawings. Process output 19 can be transmitted by such remotely located or unmanned computers to a central data storage and analysis facility 20. The detector instrument used at each location may be custom tailored to the key spectral region of interest (high optical throughput, custom grating and detector array, etc.) at that location. Further it may be desirable to ensure that, along with certain specific spectral regions that may be unique to each location; each location may also be configured to collect a common sample baseline data set to permit proofing of the data retrieved.

As described herein, the system of the present invention may include but not be limited the following elements or the functional equivalent. These elements may be related or interoperate in the following exemplary fashion. It is not intended to limit the present application to these particular interconnections, relationships or interoperability. These are described herein to illustrate the basic arrangement and operation of the system and method of the present invention and it is anticipated that persons of ordinary skill in the relevant technical area will understand additional elements and relationship between the same.

It will be seen that the telescope 14 and instrument sensor package 13 is used to acquire high resolution spectrum data in a key spectral absorption region for a molecular species of interest.

The data processor 16 defines the computer and special software compare the acquired spectrum data including but not limited to detailed line absorption depths, widths, and shapes in the "key" regions of the measured spectrum and then may extract a vertical profile of the absorber molecules under study as will be understood by those skilled in the art. The slant path high resolution transmission calculations were made with the custom line-by-line multilayer propagation model of the lower atmosphere (0 to 100 km altitude). This model was developed by the applicant and validated with the field measurements (Dowling 1977, Dowling 1978). The molecular absorption line widths, strengths, and positions are from the widely available 1996 revision of the AFGL Line Atlas (McClatchey 1973). The program model includes good temperature corrections and both collisional and velocity line broadening effects to permit applicability to the upper atmosphere as well as to sea level. The search routine performs trial and error iterations between the measured spectra and an estimator or profile-generated spectra to achieve a best fit. Absorption line shapes are calculated for accuracy at distances near and far from line center over the entire spectrum. If a measured vertical temperature is not available via balloon sonde or other source, then the T-profile can be retrieved from the high resolution test spectra using this search methodology (same procedure as above) and a different spectral region for the T (temperature) parameter.

1. Dowling, J. A., Naught, K. M., Horton R. F., Hanley S. T., Curcio, J. A., Garcia, D. H., Gott, C. O., Agambar, W. L. (1977). Atmospheric transmission Field Experiments Using IR Lasers, Fourier Transform Spectroscopy and Gas Filter Correlation Techniques. NRL Reports of Progress 4142
2. Dowling, J. A., Horton, R. F., Hanley, S. T., Naught, K. M. (1978). High Resolution Field measurement of Atmospheric Transmission. SPIE Proceedings 142, 25
3. McClatchey, R. A., Benedict, W. S., Clough, S. A., Burch, D. E., Calfee, R. F., Fox, K., Rothman, L. S., Garing, J. S. (1973). Air force Cambridge Research laboratories Atmospheric Absorption Line Parameters Compilation AFCRL-TR-0096

A published molecular absorption line atlas (such as the widely 1994 revision of the AFGL Line Atlas) containing line positions, strengths, and widths may be used in the specialized profile retrieval software as it works to determine the vertical profile of the molecular species of interest.

In operation, the radiation source 10, such as the sun (or any full spectrum emitter at high altitude) may be used for transmission through the atmospheric column 12. The high resolution spectrograph 15 or fast scanning interferometer (or equivalent instrument) will preferably be able to fully and accurately resolve the molecular absorption spectrum. This spectrum may then be input to the data processor 16 defined of computer enabled software for comparison against a specialized software generated synthetic spectrum. The details of absorption line width, depth, and fine-detail shape of absorption side-walls may allow retrieval of determination of any amounts of absorber molecules of interest occurring at each elevation (using, for example but not limited to, known barometric pressure and temperature versus altitude.) The objective of this work is to extract vertical density distributions of an atmospheric constituent molecule based on absorption detail (<0.1 cm-1) contained in measured slant-path transmission spectra. Examples of atmospheric transmission spectra measured over long path and the associated hardware are presented in (Dowling 1977) and (Dowling 1978) using a scanning Michelson Fourier Transform interferometer. The measured transmissions must traverse the vertical height of interest for the profile retrieval as for example with slant path solar spectroscopy providing ground to top of atmosphere or alternatively ground to a light source positioned at elevation. The steps used in the retrieval are to perform a high resolution line-by-line calculation of slant path transmission (McClatchey 1973, Dowling 1977) using a Mid Latitude profile as a starting point. Next the point-by-point differences between the calculated and measured spectra are noted. Adjustments are made to the initial Mid Latitude estimator profile and a new calculated slant path spectrum is made. Then point-by-point differences between measured and calculated absorption detail are again examined. When the new point-by-point differences between measured and (most recently adjusted) estimator spectra are reduced, then the most recent adjusted profile (with improvement to fit) becomes the new estimator reference. This process is repeated until no further improvement can be made between calculated and measured transmission curves, at which point a vertical profile has been retrieved. The temperature and pressure dependences of the vib rational and rotational band structure dictate the positioning of the molecule concentrations along the vertical viewing path. Using this methodology, key spectral regions (spectral Keys) have been identified that permit accurate retrieval of water vapor profiles from transmission spectra without interference from other atmospheric absorbing species.

It will thus be seen that by utilization of an optical telescope 14 adapted to collect the source radiation on to a spectrometer or spectrograph 15 as detection hardware. The resulting measurement of high resolution of spectra as noted as input into data processor 16 enabled computer for comparison to line-by-line spectral calculations based on the hereinbefore defined line atlas perimeters. It will also be evident that trial vertical profiles of atmospheric constituent molecule under study may be iterated or varied until a match is achieved between measured and calculated high resolution transmission spectra at which point the retrieved molecular constituent profile 17 may be achieved.

As noted, it is anticipated that other sources of radiation such as a search light (not shown) may be placed as an alternate source on a mountain instead of relying on passive solar radiation and this sort of terrestrial radiation source may be used to derive a partial vertical (not to top of atmosphere) profile of the desired molecular constituent. This use of more active radiation sources may afford stationary path and co-additive measured spectra to allow reduced noise in the measured spectra.

It will be evident that the sensor package 13 detector may be any high resolution device capable of fully resolving the molecular absorption features within the key spectral region for the molecule under study. Accordingly, the fast scan of the key spectral range is advantageous so that conditions are not changing during measurement.

The system and methodology of the present invention 10 may allow retrieval of any atmospheric component profile of interest (e.g., C02 (greenhouse gas), CH4 (methane), O3 (ozone layer), H20, HDO etc.), as well as any atmospheric thermal profiles, and to monitor changes in those components on interest.

Referring now back to FIG. 4 of the drawings, the system and method of the present invention can be used to provide resident sensor packs at remote locations 18 and permit gathering of data independent of the present of human workers to operate or maintain the unit on a daily basis. The use of computerized specialized software can be optimized for processed data input to be transmitted to a central data storage and analysis facility 20 by any suitable tele-communication protocol or network 19. The detector instrument utilized can be custom-tailored to key spectral regions of interest, such as high optical output custom grating and detector array, etc. It will thus be seen that a new and novel system and method for retrieving mass density distributions and thermal profiles from the atmosphere to identify molecular constituents that absorb spectral energy has been illustrated and described, and it will be apparent to those skilled in the art that various changes and modifications may be made thereto without departing from the spirit of the invention.

Therefore I claim:

1. An atmospheric constituent molecule detection measuring and comparison system comprising:
    a radiation generating element projecting radiation through at least a portion of the Earth's atmosphere;
    a radiation gathering device configured to gather radiation from the radiation generating element after the radiation has passed through a defined at a least a portion of the Earths atmosphere;
    a radiation sensing device configured to detect and receive radiation gathered by the radiation gathering device and generate spectrum data readings based on extract vertical density distribution for one or more constituents molecules within atmosphere column through which the radiation passed, said generated data corresponds to the amount of said radiation that was absorbed by the constituent molecules;
    computing means including custom software with at least one known spectral line atlas table relating to one or more constituent molecules for comparison therewith, said computing means further comprising a computer for receiving the generated data readings from said radiation sensing device comparing said generated data readings with the known spectral line atlas table to determine an elevation and molecular density profile for the one or more constituent molecules within at least a portion of the Earth's atmosphere.

2. The atmospheric constituent molecular detection measuring and comparison system set forth in claim 1 wherein said radiation generating element comprises the sun.

3. The atmospheric constituent molecular detection measuring and comparison system set forth in claim 1 wherein said radiation gathering device comprises,
    an optical telescope in communication with a high resolution spectrograph.

4. The atmospheric constituent molecular detection system set forth in claim 1 wherein said computer custom software comprises,
    a software generated synthetic spectrum for comparison with acquired spectrum data measurements from said radiation gathered device.

5. The atmospheric constituent molecular detection system set forth in claim 1 wherein said acquired spectrum data readings comprises,
    detailed line absorption depths, widths and shapes in key regions of said measured spectrum and extracted vertical profiles of said absorbed molecules.

6. The atmospheric constituent molecular detection measuring system set forth in claim 1 wherein said computer software further comprises,
    at least one known molecular absorption spectral line atlas, said atlas containing establish line positions, depths and widths, for use with said software to determine vertical profile of molecular species of interest comparison.

* * * * *